United States Patent [19]

Pinke

[11] 4,210,608
[45] * Jul. 1, 1980

[54] MANUFACTURE OF LINEAR PRIMARY ALDEHYDES AND ALCOHOLS

[75] Inventor: Paul A. Pinke, Des Plaines, Ill.

[73] Assignee: UOP Inc., Des Plaines, Ill.

[ * ] Notice: The portion of the term of this patent subsequent to May 25, 1993, has been disclaimed.

[21] Appl. No.: 638,881

[22] Filed: Dec. 8, 1975

Related U.S. Application Data

[63] Continuation-in-part of Ser. No. 469,162, May 13, 1974, Pat. No. 3,959,386.

[51] Int. Cl.² ............................................. C07C 45/10
[52] U.S. Cl. .................................. 568/451; 568/454; 568/909
[58] Field of Search ................. 260/604 HF, 632 HF; 469/162

[56] References Cited

U.S. PATENT DOCUMENTS

| | | | |
|---|---|---|---|
| 3,352,924 | 11/1967 | Gladrow | 260/604 HF |
| 3,644,445 | 2/1972 | Kroll | 260/604 HF |
| 3,733,362 | 5/1973 | Biale | 260/604 HF |
| 3,880,938 | 4/1975 | Massie | 260/632 HF |
| 3,937,742 | 2/1976 | Yoo | 260/632 HF |

Primary Examiner—Werren B. Lone
Attorney, Agent, or Firm—James R. Hoatson, Jr.; Robert W. Welch; William H. Page, II

[57] ABSTRACT

Linear primary aldehydes and alcohols are produced from linear monoolefinic hydrocarbons. The monoolefinic hydrocarbon is treated in admixture with carbon monoxide and hydrogen and in contact with an aluminum catalyst and a Group VIII metal hydroformylation catalyst.

11 Claims, No Drawings

MANUFACTURE OF LINEAR PRIMARY ALDEHYDES AND ALCOHOLS

CROSS-REFERENCE TO RELATED APPLICATIONS

This is a continuation-in-part application of a copending application Ser. No. 469,162, filed May 13, 1974 issued as U.S. Pat. No. 3,959,386 on May 25, 1976.

This invention relates to the conversion of linear or straight chain monoolefinic hydrocarbons to linear primary aldehydes and alcohols. It is frequently desirable to manufacture linear primary aldehydes and/or alcohols utilizing available linear monoolefinic hydrocarbon feed stocks comprising one or more species characterized by internal unsaturation. The manufacture of aldehydes and/or alcohols by reacting said monoolefinic hydrocarbons with carbon monoxide and hydrogen in contact with what has come to be known as a hydroformylation catalyst, for example, dicobalt octacarbonyl, is an old and well-known process. One basic and serious disadvantage of the hydroformylation process has been the inability to convert linear internally unsaturated, monoolefinic hydrocarbons to linear terminal aldehydes and/or alcohols to the substantial exclusion of other isomeric forms thereof. Even in the case of terminal olefins, the product is, at best, only 80–90% linear primary aldehydes and/or alcohols. By way of illustration, when the linear monoolefinic hydrocarbon starting material is an internal olefin, the aldehyde and/or alcohol product will typically contain one more carbon atom than the olefinic starting material—a hydrogen radical having attached itself to one of the double bonded carbon atoms, with a carbonyl radical adding to the other of said carbon atoms, and the product will invariably exhibit a branch chain configuration. It is apparent, that even with respect to a terminal monoolefinic starting material, a substantial portion of the product will have a branched chain configuration resulting from the addition of said carbonyl radical to an internal carbon atom.

It is an object of this invention to provide an improved method for the conversion of linear monoolefinic hydrocarbons to linear primary aldehydes and/or alcohols, said method being particularly adapted to the conversion of internal olefins to said aldehydes and/or alcohols. The products of the method of this invention are extensively employed as solvents in medicinal and cosmetic preparations, perfume manufacture, as extractants or solvents for materials in lacquers and varnishes, as alkylating agents in the preparation of synthetic biodegradable detergents, and as intermediates in organic synthesis, for example, in the manufacture of plasticizers for synthetic resins.

In one of its broad aspects, the present invention embodies a method of converting linear monoolefinic hydrocarbons to linear primary aldehydes and/or alcohols which comprises treating said monoolefinic hydrocarbon in admixture with hydrogen and carbon monoxide and in contact with an aluminum catalyst selected from the group consisting of aluminum, alkyl aluminum and alkyl aluminum hydride, and in contact with a soluble Group VIII metal hydroformylation catalyst at a temperature of from about 25° to about 400° C. and at a pressure of from about 14 to about 4000 pounds per square inch.

One of the more specific embodiments of this invention is in a method of converting octene-1 to nonanal and 1-nonanol which comprises treating said octene-1 in admixture with hydrogen and carbon monoxide and in contact with triethylaluminum and tributylphosphine cobalt chloride at a temperature of from about 50° to about 400° C. and at a pressure of from about 500 to about 4000 pounds per square inch.

Other objects and embodiments of this invention will become apparent in the following detailed specification.

Linear monoolefinic hydrocarbons particularly suitable for use in accordance with the method of this invention include butene-1, butene-2, pentene-1, pentene-2, hexene-1, hexene-2, hexene-3, heptene-1, heptene-2, heptene-3, octene-1, octene-2, octene-3, nonene-1, nonene-2, nonene-3, decene-1, decene-2, decene-3, decene-4, decene-5, undecene-1, undecene-2, undecene-3, undecene-4, undecene-5, dodecene-2, dodecene-3, dodecene-4, dodecene-5, tridecene-1, tridecene-2, tridecene-3, tetradecene-1, tetradecene-2, tetradecene-3, pentadecene-6, heptadecene-6, and the like, as well as mixtures thereof.

In accordance with the method of this invention, the monoolefinic hydrocarbon starting material is treated in admixture with hydrogen and carbon monoxide and in contact with an aluminum catalyst and a soluble Group VIII metal hydroformylation catalyst. The aluminum catalyst is suitably employed in from about a 0.1 to about a 1.0 molar ratio with the monoolefinic hydrocarbon starting material. Metallic aluminum, when employed as the catalyst, is preferably in a finely divided form. The alkyl aluminum and alkyl aluminum hydride catalyst for use herein may be represented by the general formula $AlR_3$ wherein at least one of the R substituents is an alkyl radical with the remaining R substituents being a hydrogen or an alkyl radical, said alkyl radical in either case containing up to about 12 carbon atoms. Preferred alkyl aluminum and alkyl aluminum hydrides for use in accordance with the method of this invention include trimethylaluminum, triethylaluminum, tri-n-propylaluminum, triisopropylaluminum, tri-n-butylaluminum, triisobutylaluminum, tri-n-pentylaluminum, tri-n-hexylaluminum, tri-n-heptylaluminum, tri-n-octylaluminum, dimethylaluminum hydride, diethylaluminum hydride, di-n-propylaluminum hydride, diisopropylaluminum hydride, di-n-butylaluminum hydride, diisobutylaluminum hydride, di-n-pentylaluminum hydride, di-n-hexylaluminum hydride, di-n-hepthylaluminum hydride, di-n-octylaluminum hydride, methylaluminum dihydride, ethylaluminum dihydride, and the like. Triethylaluminum is a particularly suitable alkyl aluminum for use in the present invention.

The Group VIII metal hydroformylation catalyst, that is, iron, nickel, cobalt, platinum, palladium, rhodium, osmium and iridium hydroformylation catalysts employed herein are known to the art. Suitable hydroformylation catalysts include iron chloride, cobalt chloride, nickel dichloride, ruthenium trichloride, rhodium trichloride, palladium chloride, osmium chloride, iridium chloride, platinum chloride, nickel acetylacetonate, rhodium acetylacetonate, palladium acetylacetonate, osmium acetylacetonate, iridium acetylacetonate, nickel dicyclo-1,5-octadiene, ruthenium dicyclo-1,5-octadiene, rhodium dicyclo-1,5-octadiene, iridium dicyclo-1,5-octadiene, palladium dicyclo-1,5-octadiene, platinum dicyclo-1,5-octadiene, etc. Preferred hydroformylation catalysts include the aforementioned dicobalt octacarbonyl, and also bis(tributylphosphine)

nickel chloride, triphenylphosphine rhodium trichloride, tributylphosphine cobalt chloride, tributylphosphine ruthenium chloride, bis-cyclooctadienyl nickel, and the like. Other hydroformylation catalysts which can be utilized include the Group VIII metal, and especially the iron group metal, carbonyls, for example, cobalt tetracarbonyl, nickel carbonyl, iron pentacarbonyl, etc., and also carbonyl derivatives such as hydrocarbonyls or phosphine-substituted carbonyls such as have heretofore been disclosed in the art. Catalyst stability as well as selectivity may be improved through the use of a stabilizing ligand based on either phosphorous, nitrogen, or arsenic. Some examples would include the trialkyl, triaryl and mixed alkyl and aryl derivatives such as trimethyl, triethyl, tripropyl, tributyl, tricyclohexyl, triphenyl, dialkylphenyl, alkyldiphenyl, phosphines, amines, or arsines.

The hydrogen and carbon monoxide reactants employed herein are suitably employed in about a 1:1 molar ratio, each of said reactants being present in at least about an equimolar ratio with the monoolefinic hydrocarbon. As heretofore indicated, the reaction mixture is heated, a temperature of from about 25° to about 400° being effective to promote the desired reaction although temperatures in the higher range, say from about 50° to about 400°, are preferable. Reaction conditions further include a pressure of from about 14 to about 4000 pounds per square inch, preferably an elevated pressure, for example, a pressure of from about 500 to about 4000 pounds per square inch.

The present invention can be effected in any conventional or otherwise convenient manner and may comprise a batch or a continuous type of operation. For example, in a batch type of operation, the selected monoolefinic hydrocarbon or hydrocarbons, alkyl aluminum compound and Group VIII metal hydroformylation catalyst are charged to a suitable high pressure reaction vessel embodying adequate heating and mixing means. The vessel is then sealed, preferably flushed with dry nitrogen, and then brought to a desired initial pressure by means of the hydrogen and carbon monoxide reactants charged thereto. The vessel contents are then heated at reaction temperature and, since hydrogen and carbon monoxide are consumed in the reaction, the progress of the reaction can be monitored by observing the pressure gradient. Or it may be desirable to maintain a constant pressure by the continuous or intermittent addition of hydrogen and/or carbon monoxide to the reaction vessel. Upon completion of the reaction, the reactor is cooled to room temperature and excess hydrogen and carbon monoxide discharged therefrom. The desired reaction products are recovered from the reaction mixture by any suitable means known to the art, including distillation methods.

In a continuous type of operation, the reactants and catalysts are admixed and continuously charged, or individually charged, to a reactor maintained at suitable conditions of temperature and pressure. The reactor may comprise an unpacked vessel, for example a straight or cogelled tubular reactor, or it may contain an adsorbent packing material such as firebrick, alumina, dehydrated bauxite, and the like. The reactor effluent is withdrawn at a rate which will insure an adequate residence time therein, and unconverted reactants and catalysts are separated and recycled to the reactor as a portion of the reactor feed stock.

Examples of primary aldehydes and primary alcohols which may be prepared according to the process of this invention will include butanol, pentanol, hexanol, heptanol, octanol, nonanol, decanol, pentanal, hexanal, heptanal, octanal, nonanal, decanal, undecanal, dodecanal, tridecanal, tetradecanal, pentadecanal, and the like.

The following examples are presented in illustration of the method of this invention and are not intended as an undue limitation on the generally broad scope of the invention as set out in the appended claims.

EXAMPLE I

In the manufacture of nonanal (n-nonylaldehyde) and 1-nonanol, 11.2 grams of octene-3, 0.2 grams of triethylaluminum and 0.3 grams of tributylphosphine cobalt chloride are placed in a glass liner and inserted in a rotatable steel autoclave of about 850 cc capacity, the autoclave being thereafter flushed with dry nitrogen and sealed. The autoclave is then pressured to about 500 psig with hydrogen, and then to about 1000 psig with carbon monoxide. As the autoclave is rotated, the contents are heated at a temperature ranging from 150° to 160° C. over a 24 hour period. After cooling to room temperature, unreacted hydrogen and carbon monoxide are vented to the atmosphere, and the nonanal and 1-nonanol products separated from the catalyst substantially free of branched chain isomers thereof.

EXAMPLE II

In this example, 13 grams of a liquefied mixture of butene-1, butene-2, pentene-1, pentene-2, hexene-1, and hexene-2 is charged to a glass liner together with 0.4 grams of diisopropylaluminum hydride and 0.1 grams of triphenylphosphine rhodium chloride, and the glass liner inserted in an 850 cc rotatable steel autoclave. The autoclave is flushed with dry nitrogen, pressured to 200 psig with hydrogen, and thereafter to 300 psig with carbon monoxide. After rotating the autoclave for about 18 hours at about 125° C. the autoclave is cooled to room temperature and unreacted hydrogen and carbon monoxide vented to the atmosphere. The alkanal and alkanol reaction products are separated from the catalyst substantially free of branched chain isomers thereof.

EXAMPLE III

The conversion of an n-octene feed stock to nonanal and 1-nonanol is effected by charging about 12 grams of the n-octene, 1.0 grams of triisobutylaluminum, and 0.1 grams of dicobalt octacarbonyl to a glass lined, nitrogen-flushed, rotatable sealed autoclave, the autoclave being subsequently pressured to about 500 psig with hydrogen and then to about 1000 psig with carbon monoxide. The autoclave contents are then heated at a temperature ranging from about 150° to about 160° C. over a 24 hour period, after which the autoclave is cooled to room temperature and unreacted hydrogen and carbon monoxide discharged therefrom. The nonanal and nonanol products are separated from the catalyst substantially free of branched chain isomers thereof.

EXAMPLE IV

In the manufacture of a linear primary octanal and octanol mixture, approximately 12 grams of n-heptenes, 0.2 grams of diethylaluminum hydride and about 0.3 grams of tributylphosphine ruthenium chloride are placed in a glass-lined, nitrogen-flushed, rotatable steel autoclave. The autoclave is pressured to about 500 psig with hydrogen and then to about 1000 psig with carbon monoxide. As the autoclave is rotated, contents are heated at a temperature ranging from 150° to 160° C. over a 24 hour period. After cooling to room temperature, unreacted hydrogen and carbon monoxide are vented to the atmosphere, and the octanal and 1-octanol products separated from the catalyst substantially free of branched chain isomers thereof.

I claim as my invention:

1. A method of converting linear internal monoolefinic hydrocarbons possessing from 4 to 16 carbon atoms to linear primary aldehydes and alcohols which comprises treating said internal monoolefinic hydrocarbons in admixture with hydrogen and carbon monoxide and in contact with an aluminum catalyst selected from the group consisting of metallic aluminum, alkyl aluminum and alkyl aluminum hydride, and in contact with a Group VIII metal hydroformylation catalyst at a temperature of from about 25° to about 400° C. and at a pressure of from about 14 to about 14,000 pounds per square inch.

2. The method of claim 1 further characterized in that said temperature is from about 50° to about 400° C.

3. The method of claim 1 further characterized in that said pressure is from about 500 to about 4000 pounds per square inch.

4. The method of claim 1 further characterized in that said aluminum catalyst is a finely divided aluminum metal.

5. The method of claim 1 further characterized in that said aluminum catalyst is a trialkyl aluminum.

6. The method of claim 1 further characterized in that said aluminum catalyst is a dialkyl aluminum hydride.

7. The method of claim 1 further characterized in that said aluminum catalyst is triethylaluminum.

8. The method of claim 1 further characterized in that said aluminum catalyst is diethylaluminum hydride.

9. The method of claim 1 further characterized in that said hydroformylation catalyst is dicobalt octacarbonyl.

10. The method of claim 1 further characterized in that said hydroformylation catalyst is triphenylphosphine rhodium chloride.

11. The method of claim 1 further characterized in that said hydroformylation catalyst is tributylphosphine ruthenium chloride.

* * * * *